United States Patent [19]

Burval et al.

[11] Patent Number: 5,468,718
[45] Date of Patent: Nov. 21, 1995

[54] LIQUID, PHYTOACTIVE COMPOSITIONS AND METHOD FOR THEIR PREPARATION

[75] Inventors: Jan Burval, San Rafael; Jimmy H. Chan, Martinez, both of Calif.

[73] Assignee: ICI Americas Inc., Wilmington, Del.

[21] Appl. No.: 422,752

[22] Filed: Apr. 13, 1995

Related U.S. Application Data

[63] Continuation of Ser. No. 90,445, Jul. 12, 1993, abandoned, which is a continuation of Ser. No. 174,295, Mar. 28, 1988, abandoned, which is a continuation-in-part of Ser. No. 789,854, Oct. 21, 1985, abandoned.

[51] Int. Cl.$^6$ ............................ A01N 57/20; A01N 57/12
[52] U.S. Cl. ...................... 504/206; 504/116; 71/DIG. 1
[58] Field of Search ...................................... 504/116, 206

[56] References Cited

U.S. PATENT DOCUMENTS

| | | | |
|---|---|---|---|
| 3,219,656 | 11/1965 | Boettner et al. | 536/18.3 |
| 3,288,846 | 11/1966 | Irani et al. | 260/500 |
| 3,455,675 | 7/1969 | Irani et al. | 71/86 |
| 3,556,762 | 1/1971 | Hamm et al. | 71/86 |
| 3,598,865 | 8/1971 | Lew et al. | 536/4.1 |
| 3,799,758 | 3/1974 | Franz | 504/206 |
| 3,853,530 | 12/1974 | Franz | 504/165 |
| 3,868,407 | 2/1975 | Franz et al. | 504/206 |
| 3,888,915 | 6/1975 | Alt | 504/203 |
| 3,933,946 | 1/1976 | Gaertner | 504/203 |
| 3,948,975 | 4/1976 | Franz | 504/206 |
| 3,970,695 | 7/1976 | Rueppel | 504/206 |
| 3,988,142 | 10/1976 | Franz | 504/206 |
| 3,991,095 | 11/1976 | Gaertner | 504/205 |
| 3,996,040 | 12/1976 | Franz | 504/203 |
| 4,025,331 | 5/1977 | Leber | 504/202 |
| 4,047,927 | 9/1977 | Gaertner | 504/206 |
| 4,062,669 | 12/1977 | Franz | 504/203 |
| 4,084,953 | 4/1978 | Franz | 504/203 |
| 4,119,430 | 10/1978 | Gaertner | 504/206 |
| 4,120,689 | 10/1978 | Dutra | 504/206 |
| 4,140,513 | 2/1979 | Prill | 504/206 |
| 4,147,719 | 4/1979 | Franz | 562/17 |
| 4,159,901 | 7/1979 | Beestman et al. | 252/395 |
| 4,180,394 | 12/1979 | Franz | 504/195 |
| 4,197,254 | 4/1980 | Gaertner | 560/20 |
| 4,203,756 | 5/1980 | Gaertner | 504/206 |
| 4,251,257 | 2/1981 | Gaertner | 71/86 |
| 4,261,727 | 4/1981 | Dutra | 504/205 |
| 4,312,662 | 1/1982 | Gaertner | 504/205 |
| 4,315,765 | 2/1982 | Large | 504/206 |
| 4,322,239 | 3/1982 | Dutra et al. | 504/203 |

FOREIGN PATENT DOCUMENTS

| | | |
|---|---|---|
| 18744 | of 0000 | Australia . |
| 22666 | 1/1981 | European Pat. Off. . |
| 2129203 | 5/1984 | United Kingdom . |
| 8403607 | 9/1984 | WIPO . |

OTHER PUBLICATIONS

U.S. Statutory Invention Registration No. H224, filed May 30, 1985, A. E. Staley Manufacturing Company.
Wyrill, J. B. and O. C. Burnside, "Glyphosate Toxicity to Common Milkweed and Hemp Dogbane as Influenced by Surfactants", Weed Science, vol. 25; 275–287, 1977.
Technical Notes by Rohm & Haas Company.
Leaver et al., "Dual Role of a etc" (1979); CA91:6321F (1979).
Reffert et al. "Stabilizing Poly(Phenyline ether) Solutions", (1985); CA102:204897g (1985).
Maringer et al., "Stabilized Polymer, etc." (1982) CA97:145817 (1982).
Maeda et al. "Protective Materials for etc." (1978) CA90:137802 (1979).

(List continued on next page.)

*Primary Examiner*—Allen J. Robinson
*Assistant Examiner*—B. Bembenick
*Attorney, Agent, or Firm*—Joel G. Ackerman

[57] ABSTRACT

A liquid phytoactive composition comprising (a) an N-phosphonomethyl-N-carboxymethyl compound; (b) one or more liquid surfactants; (c) a dispersing medium for said N-phosphonomethyl-N-carboxymethyl compound; and (d) inert adjuvants therefor.

12 Claims, No Drawings

U.S. PATENT DOCUMENTS

| | | | |
|---|---|---|---|
| 4,341,549 | 7/1982 | Large et al. | 504/206 |
| 4,384,880 | 5/1983 | Large | 501/206 |
| 4,395,374 | 7/1983 | Dutra et al. | 549/221 |
| 4,397,676 | 8/1983 | Bakel | 504/206 |
| 4,405,531 | 9/1983 | Franz | 562/17 |
| 4,411,693 | 10/1983 | LeClair et al. | 504/341 |
| 4,414,158 | 11/1983 | Thummel et al. | 504/190 |
| 4,437,874 | 3/1984 | Large | 504/206 |
| 4,440,562 | 4/1984 | Prill | 504/127 |
| 4,441,919 | 4/1984 | Albrecht et al. | 504/330 |
| 4,472,189 | 9/1984 | Prisbylla | 504/192 |
| 4,481,026 | 11/1984 | Prisbylla | 504/190 |
| 4,483,781 | 11/1984 | Hartman | 252/95 |
| 4,487,724 | 12/1984 | Felix | 562/18 |
| 4,507,250 | 3/1985 | Bakel | 502/17 |
| 4,666,500 | 5/1987 | Dutra et al. | 71/87 |
| 4,931,080 | 6/1990 | Chan et al. | 504/192 |

OTHER PUBLICATIONS

Schoenbeck et al., "Pre–formed Substances, etc." (1979) CA87:180607f (1977).

Charavas et al., "Phytochemical relationships" (1980) CA 94:27777m (1981).

Gabriele et al. "Influence of light, etc." (1982) CA98:18150g (1983).

U.S. Statutory Invention Registration No. H224, filed May 30, 1985, A. E. Stanley Mfg. Company (1987).

Wyrill, J. B. et al., "Glyphosate Toxicity to Common Milkweed and Hemp. Dogbane as Influenced by Surfactants", Weed Science, vol. 25, 275–287, 1977.

Federal Register, vol. 39, No. 78, Apr. 22, 1974.

*Weed Research*, 1980, vol. 20, pp. 139–146, "Effects of Ammonium Sulphate and Other Additives Upon the Phytotoxicity of Glyphosate to *Agropyron Repens* (L) Beauv," D. J. Turner et al.

*Can J. Plant Sc.*, 61:pp. 391–400 (Apr. 1981), "Influence of Non–ionic Surfactants, Ammonium Sulphate, Water Quality and Spray Volume on the Phytotoxicity of Glyphosate," P. A. O'Sullivan et al.

*Weed Research*, 1985, vol. 25, pp. 81–86, "Basis for Changes in Glyphosate Phytotoxicity to Barley by the Non–ionic Surfactants Tween 20 and Renex 36," J. T. O'Donovan et al.

Weeds, vol. 12, 1964, pp. 251–255, "Surfactant Enhancement of Herbicide Entry," L. L. Jansen.

Weeds, vol. 13(2), 1965, pp. 117–123, "Effects of Structural Variations in Ionic Surfactants on Phytotoxicity and Physical–Chemical Properties of Aqueous Sprays of Several Herbicides," L. L. Jansen.

Agri. Food Chem., 29, pp. 227–230 (1981), "Survey for Surfactant Effects on the Photodegradation of Herbicides in Aqueous Media," F. S. Tanaka et al.

Grass Weeds in Cereals, 1981, pp. 167–171, "The Effects of Additives on the Control of Agropyron Repens with Glyphosate," D. J. Turner.

"Adjuvants for Herbicides" by Weed Science Society, 1982.

"Encyclopedia of Chemical Technology," Kirk–Othmer, vol. 22, 3rd Edition, 1983, Chapter on Surfactants.

McCutcheon's Emulsifiers and Detergents, 1983, pp. 32, 51, 169, 175 and 180.

LIQUID, PHYTOACTIVE COMPOSITIONS AND METHOD FOR THEIR PREPARATION

This application is a continuation of application Ser. No. 08/090,445, filed Jul. 12, 1993 (abandoned), which is a continuation of application Ser. No. 07/174,295 filed on Mar. 28, 1988 (abandoned), which is a continuation-in-part of application Ser. No. 06/789,854, filed Oct. 21, 1985, now abandoned.

BACKGROUND OF THE INVENTION

This invention relates to novel, liquid phytotactive compositions comprising phytoactive compounds containing the moiety:

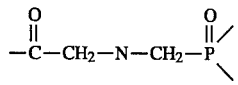

plus certain nonionic surfactants, and to methods of use of such compositions.

The phytoactive compounds containing the moiety set forth above as Formula I are designated herein as N-phosphonomethyl-N-carboxymethyl compounds or "PMCM" compounds. These compounds and the moiety of Formula I will be further defined and illustrated hereinafter. For convenience, the phytoactive compounds containing the moiety of Formula I will hereinafter be designated PMCM compounds.

THE PRIOR ART

A large number of phytoactive PMCM compounds are known in the art. The term "phytoactive" as used in describing this invention means effective as a plant growth regulator, as a herbicide, as a defoliant or the like. Illustrative of such PMCM compounds and their use are:

U.S. Pat. No. 3,455,675, Irani, Jul. 15, 1969, entitled "Aminophosphonate Herbicides";

U.S. Pat. No. 3,556,762, Hamm, Jan. 19, 1971, entitled "Increasing Carbohydrate Deposition in Plants with Aminophosphonates";

U.S. Pat. No. 4,405,531, Franz, Sep. 20, 1983, entitled "Salts of N-Phosphonomethylglycine";

U.S. Pat. No. 3,868,407, Franz, Feb. 25, 1975, entitled "Carboxyalkyl Esters of N-Phosphonomethylglycine;

U.S. Pat. No. 4,140,513, Prill, Feb. 20, 1979, entitled "Sodium Sesquiglyphosate";

U.S. Pat. No. 4,315,765, Large, Feb. 16, 1982, entitled "Trialkylsulfonium Salts of N-Phosphonomethylglycine;"

U.S. Pat. No. 4,481,026, Prisbylla, Nov. 6, 1984, entitled "Aluminum N-Phosphonomethylglycine and Its Use As A Herbicide";

U.S. Pat. No. 4,397,676, Bakel, Aug. 9, 1983, entitled "N-Phosphonomethylglycine Derivatives"; and International Application WO 84/03607, Chevron Research Company, Sep. 27, 1984, entitled "Glyphosate-Type Herbicidal Compositions".

These patents are illustrative and are incorporated herein by reference. Most of these patents also include descriptions of processes employed to prepare such compounds. The following patents provide additional process descriptions.

U.S. Pat. No. 3,288,846, Irani et al., Nov. 29, 1966, entitled "Process for Preparing Organic Phosphonic Acids";

U.S. Pat. No. 4,507,250, Bakel, Mar. 26, 1985, entitled "Process for Producing N-Phosphonomethylglycine Acid";

U.S. Pat. No. 4,147,719, Franz, Apr. 3, 1979, entitled "Process for Producing N-Phosphonomethylglycine"; and U.S. Pat. No. 4,487,724, Felix, Dec. 11, 1984, entitled "Process for Preparation N-Phosphonomethylglycine Salts". These patents are also incorporated herein by reference.

Certain PMCM compounds, in particular, water-soluble salts of PMCM, have been found to be especially effective as post-emergent herbicides. Such salts of PMCM, which are particularly effective as herbicidal agents, include the trimethylsulfonium salts of N-phosphonomethylglycine such as are disclosed in U.S. Pat. No. 4,315,765, the mixed alkylsulfonium salts of N-phosphonomethylglycine such as are disclosed in U.S. Pat. No. 4,437,874, and the trialkyl salts of N-phosphonomethylglycine which are disclosed in U.S. Pat. Nos. 4,384,880 and 4,345,765.

Normally, herbicidal compositions are formulated as dusts, granular compositions, liquid emulsions, or liquid concentrates. The salts of N-phosphonomethylglycine which are used as the active ingredients in herbicides are preferably formulated as liquid concentrates because they are, in fact, water-soluble and hygroscopic which makes them difficult to crystallize and isolate from water solutions. A good liquid concentrate exhibits good compatibility of the various ingredients, good heat and long term storage stability, and miscibility of the active ingredient with the liquid solvent. In addition, it should have minimum eye irration and low levels of inhalation irritation. Not all liquid concentrates containing the salts of N-phosphonomethylglycine as the active ingredient exhibit these properties.

An object of this invention therefore is to provide a phytoactive composition in the form of a liquid concentrate utilizing as the active ingredient, a PMCM compound, preferably an agriculturally acceptable salt of N-phosphonomethylglycine, and an non-ionic surfactant.

DESCRIPTION OF THE INVENTION

The present invention is directed to a liquid phytoactive formulation containing as the active ingredient, an N-phosphonomethyl-N-carboxymethyl compound dissolved or dispersed in a suitable medium, and a liquid nonionic surfactant. The formulation is dilutable by water or water-containing liquid before application in the field.

The formulation of this invention has the advantage that it can contain a high amount of active ingredient, is thermally stable over a wide temperature range, is compatible with and dilutable in both hard and soft water, and is also compatible and dilutable with a nitrogeneous fertilizer solution, and is minimally irritable to the eyes. Also, the formulation of this invention is stable upon aging over months of storage, over a wide temperature range. In addition, the nonionic surfactants are derived from naturally occurring products and are readily broken down by microorganisms.

The embodiment of this invention therefore is a novel phytoactive composition comprising:

(a) a liquid-dispersible phytoactive N-phosphonomethyl-N-carboxymethyl compound;

(b) one or more liquid nonionic surfactants;

(c) a dispersing medium for said phytoactive N-phosphonomethyl-N-carboxymethyl compound, and (d) inert adjuvants.

The method of the invention comprises applying the abovedescribed phytoactive composition to the locus where control is desired. Normally, this would be on the foliage of the weed pests to be eradicated.

DETAILED DESCRIPTION OF THE PREFERRED EMBODIMENTS

Any liquid-dispersible, phytoactive PMCM compound can be used in the compositions and processes in accordance with the invention. The term "liquid-dispersible" is used in a broad sense to encompass compounds which are soluble in a liquid as well as compounds which are merely dispersible. In preferred embodiments, the PMCM compound is liquid-soluble. In the most preferred embodiment, it is water-soluble.

The PMCM compounds may be represented by the formula

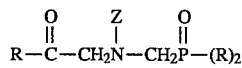

wherein

R is selected from the group consisting of halogen, —NHOH, —N($R^1$)$_2$, —$OR^2$, —$SR^2$ and —OM, where $R^1$ is independently selected from hydrogen, alkyl or hydroxyalkyl, preferably containing less than about 5 carbon atoms, alkenyl, preferably containing less than about 5 carbon atoms or phenyl moieties; $R^2$ is independently selected from hydrogen, alkyl, hydroxyalkyl or chloroalkyl, preferably containing less than about 5 carbon atoms, alkoxy, preferably containing less than about 5 carbon atoms, alkylene amine, preferably containing less than about 12 carbon atoms, phenyl or benzyl moieties; and M is selected from hydrogen and agriculturally acceptable saltforming moieties such as alkali metal, alkaline earth metal, stannic, ammonium, organic ammonium, alkyl sulfonium, alkyl sulfoxonium, alkyl phosphonium moieties or combinations thereof; and Z is hydrogen, an organic moiety or an inorganic moiety.

Representative patents disclosing at least some of such compounds include U.S. Pat. Nos. 3,799,758, 4,397,676, 4,140,513, 4,315,765, 3,868,407, 4,405,531, 4,481,026, 4,414,158, 4,120,689, 4,472,189, 4,341,549 and 3,948,975.

Representative patents disclosing PMCM compounds wherein Z is other than hydrogen include U.S. Pat. Nos. 3,888,915, 3,933,946, 4,062,699, 4,119,430, 4,322,239 and 4,084,954.

In preferred PMCM compounds, Z is hydrogen or an organic substituent. Representative organic substituents include methylene carboxylic; methylene phosphonic; methylene cyano; carbonyl, such as formyl, acetyl, benzoyl, perfluoroacyl and thiocarbonyl; ethylene, such as cyano, carbamoyl or carboxy substituted ethyl; and benzene sulfonyl substituents. Representative patents disclosing compounds where the nitrogen contains three organic substituents include U.S. Pat. Nos. 3,455,675, 3,556,762, 3,853,530, 3,970,695, 3,988,142, 3,991,095, 3,996,040, 4,047,927, 4,180,394, 4,203,756, 4,261,727 and 4,312,662. A preferred tertiary nitrogen substituted PMCM compound is N,N-bis(phosphonmethyl)glycine. Those PMCM compounds wherein Z is hydrogen are most preferred when the phytoactivity desired is herbicidal activity.

The above patents are herein incorporated by reference.

Illustrative of agriculturally acceptable salt-forming moieties represented by M, as in OM, are the alkali metals having atomic weights of from 22 through 133, inclusive, such as sodium, potassium, or rubidium; the alkaline earth metals having atomic weights of from 24 through 88 inclusive, such as magnesium or calcium; ammonium and aliphatic ammonium, wherein the aliphatic ammonium is primary, secondary, tertiary or quaternary and preferably wherein the total number of carbon atoms does not exceed more than about twelve; phenylammonium; trialkylsulfonium, preferably wherein the total number of carbons in the three alkyl substituents does not exceed more than about six, such as trimethylsulfonium, ethyl dimethylsulfonium, propyl dimethylsulfonium and the like; trialkylsulfoxonium, preferably wherein the total number of carbon atoms in the three alkyl substituent does not exceed more than about six, such as trimethylsulfoxonium, ethyl dimethylsulfoxonium, propyl dimethylsulfoxonium and the like; tetraalkylphosphonium, such as tetramethylphosphonium, ethyl trimethylphosphonium, propyl trimethyphosphonium and the like.

It should be noted that the alkaline earth metal salts, while agriculturally acceptable, provide only marginal herbicidal activity.

In preferred compositions according to this invention, M is independently selected from the above-described agriculturally acceptable salt-forming moieties and hydrogen. In more preferred compositions, M is an alkali metal, ammonium, monoalkyl ammonium or trialkysulfonium moiety. In most preferred compositions only one M is an alkali metal, ammonium, monoalkyl ammonium, or trialkylsulfonium moiety, while the two M's are hydrogen. Representative most preferred compositions include isopropylamine N-phosphonomethylglycine, trimethylsulfonium N-phosphonomethylglycine and sodium sesqui-N-phosphonomethylglycine. Combinations of two or more PMCM compounds can be employed in the compositions and processes in accordance with the invention.

The liquid nonionic surfactants used as one of the essential components of the herbicidal compositions of the invention, for example, can be any one of the following specific compounds: Al-1685 and Al-2042—mixed alcohol glucosides, sold by ICI; Emcol D-7533 and Witcamide 272 (a modified alkanolmide), sold by Witco Chemical Company; Staley APG 91-3, Staley APG 91-1, Staley APG 23-1, and Staley APG 23-3, all alkyl polyglycosides sold by Staley Corporation; and Crodesta SL-40, a monococoate sold by Croda Inc. A typical APG surfactant has the repeating structural formula

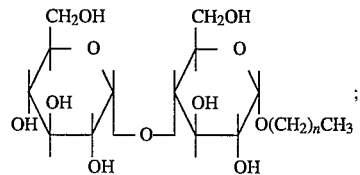

and Pluronic F-108 which is an ethylene oxide-propylene oxide block copolymer.

Any two (or more) of the above nonionic surfactants may be mixed in various ratios and used in the herbicidal composition to achieve greater physical surfactant characteristics than each alone. An example is the combination of AL-1685 and APG 91-3 in a 60:40 or 70:30 ratio.

In addition to the foregoing, inert adjuvants can also be incorporated into the compositions of this invention in order to provide for a more satisfactory formulation. Such inert adjuvants include antifoaming agents, preferably dimethylpolysil oxane, fumed silicas as a thickener, and optionally water.

The weight percentage of the PMCM active ingredient in the liquid concentrates of this invention can range from about 10 to about 70% by weight, preferably from about 30 to about 40% by weight, and most preferably from about 38 to about 42% by weight.

The nonionic surfactants used in the compositions of this invention can range from about 5 to about 40% by weight, preferably from about 15 to about 30% by weight, and most preferably from about 15 to about 25% by weight.

The quantity of inert adjuvant used in the compositions of this invention an range from about 0.5 to about 10% by weight, preferably from about 1 to about 5%, and most preferably from about 1 to about 3% by weight. Water or other liquid medium makes up the balance of the liquid concentrate. It can range from about 10 to about 70% by weight, preferably from about 20 to about 50% by weight.

The phytoactive compositions of the invention can be prepared by preparing a solution of the PMCM active ingredient and adding thereto the nonionic surfactant, the additives, if any, and as much additional dispersing agent as required. The preferred dispersing agent is water.

The advantages of the use of nonionic surfactant in the process and compositions of this invention are that they are generally inexpensive, readily available, low or non-irritating, often of low toxicity to mammals and generally, lower or non-foaming and since they are derived from naturally produced products are readily broken down by microorganisms.

As previously indicated, mixtures of various non-ionic surfactants, can also be used if desired.

The preferred phytotoxic compositions of this invention have a herbicidal active ingredient.

The following are examples of various formulations of the herbicidal compositions of this invention.

| | Ingredient | % by weight | (a.i.**) |
|---|---|---|---|
| 1. | X-100* (72%) | 57.2 | (41.2) |
| | AL-2042 (100%) | 10.3 | (10.3) |
| | Staley APG 91-3 (57%) | 18.1 | (10.3) |
| | water | 14.4 | |
| | | 100.0% | |
| 2. | X-100 (56%) | 73.3 | (41.2) |
| | AL-2042 (100%) | 20.6 | |
| | water | 6.1 | |
| | | 100.0% | |
| 3. | X-100 (72%) | 57.2 | (41.2) |
| | Staley APG 91-3 (57%) | 36.1 | (20.6) |
| | water | 6.7 | |
| | | 100.0% | |
| 4. | X-100 (72%) | 57.2 | (41.2) |
| | AL-1685 (100%) | 10.3 | (10.3) |
| | Staley APG 91-3 (57%) | 18.1 | (10.3) |
| | water | 14.4 | |
| | | 100.0% | |
| 5. | X-100 (57%) | 51.8 | (29.5) |
| | Staley APG 91-3 (70%) | 48.2 | (33.9) |

-continued

| | Ingredient | % by weight | (a.i.**) |
|---|---|---|---|
| | | 100.0% | |
| 6. | X-100 (57%) | 53.0 | (30.2) |
| | Staley APG 91-3 (57%) | 47.0 | (26.8) |
| | | 100.0% | |
| 7. | X-100 (57.3%) | 71.9 | (41.2) |
| | Spray dried Staley 23-3 (100%) | 20.6 | |
| | water | 7.5 | |
| | | 100.0% | |
| 8. | X-100 (72%) | 57.2 | (41.2) |
| | Staley 23-1 (53%) | 38.9 | (20.6) |
| | water | 3.9 | |
| | | 10.0 g | |
| 9. | X-100 (72%) | 57.2 | (41.2) |
| | Staley APG 23-3 (46%) | 42.8 | (19.7) |
| | | 100.0% | |
| 10. | X-100 (72%) | 57.2 | (41.2) |
| | Staley APG 91-1 (51%) | 40.4 | (20.6) |
| | water | 2.4 | |
| | | 100.0% | |
| 11. | X-100 (72%) | 57.2 | (41.2) |
| | Staley 91-3 (57%) | 36.1 | (20.6) |
| | | 6.7 | |
| | | 100.0% | |
| 12. | X-100 (57%) | 71.9 | (41.2) |
| | AL-2042 (100%) | 20.6 | |
| | water | 7.5 | |
| | | 100.0% | |
| 13. | X-100 (57%) | 54.3 | (31.2) |
| | AL-2042 (100%) | 31.2 | |
| | water | 14.5 | |
| | | 100.0% | |
| 14. | X-100 (57%) | 66.4 | (38.2) |
| | Emcol D-7533 (Witco) | 19.1 | |
| | water | 14.5 | |
| | | 100.0% | |
| 15. | X-100 (57%) | 54.3 | (31.2) |
| | Emcol D-7533 (Witco) | 31.2 | |
| | water | 14.5 | |
| | | 100.0% | |
| 16. | X-100 (57%) | 54.3 | (31.2) |
| | AL-2041 | 31.2 | |
| | water | 14.5 | |
| | | 100.0% | |
| 17. | X-100 (57%) | 63.2 | (36.3) |
| | AL-2042 | 27.3 | |
| | water | 9.5 | |
| | | 100.0% | |
| 18. | X-100 (57%) | 71.9 | (41.2) |
| | AL-1685 | 20.6 | |
| | water | 7.5 | |
| | | 100.0% | |
| 19. | X-100 (57%) | 71.9 | (41.2) |
| | Staley APG 91-3 | 20.6 | |
| | water | 7.5 | |
| | | 100.0% | |
| 20. | X-100 (57%) | 71.9 | (41.2) |
| | AL-2041 | 20.6 | |
| | water | 7.5 | |
| | | 100.0% | |
| 21. | X-100 (57%) | 71.9 | (41.2) |

| | Ingredient | % by weight | (a.i.**) |
|---|---|---|---|
| | Emcol D-7533 | 20.6 | |
| | water | 7.5 | |
| | | 100.0% | |
| 22. | X-100 (57%) | 71.9 | (41.2) |
| | Emcol D-7533 | 20.6 | |
| | water | 7.5 | |
| | | 100.0% | |
| 23. | X-100 (57.5%) | 71.7 | (41.2) |
| | APG 23-3 | 20.6 | |
| | water | 7.7 | |
| | | 100.0% | |
| 24. | X-100 (57%) | 71.9 | |
| | AI-1685 (ICI) | 20.6 | |
| | water | 7.5 | |
| | | 100.0% | |
| 25. | X-100 (57.5%) | 71.7 | (41.2) |
| | Staley APG 91-1 | 20.6 | |
| | water | 7.7 | |
| | | 100.0% | |
| 26. | X-100 (57.5%) | 71.7 | (41.2) |
| | APG 91-3 | 20.6 | |
| | water | 7.7 | |
| | | 100.0% | |
| 27. | X-100 (57.5%) | 71.7 | (41.2) |
| | Staley APG 23-1 | 20.6 | |
| | water | 7.7 | |
| | | 100.0% | |
| 28. | X-101ª (96.4%) | 1.25 | (1.20) |
| | AL-2042 | 0.63 | |
| | water | 98.12 | |
| | | 100.0% | |
| 29. | X-102ᵇ (99.5%) | 29.03 | (29.0) |
| | AL-2042 | 14.51 | |
| | water | 56.46 | |
| | | 100.0% | |
| 30. | X-103ᶜ (87.0%) | 35.26 | (30.7) |
| | AL-2042 | 15.34 | |
| | water | 49.40 | |
| | | 100.0% | |
| 31. | X-104ᵈ (98.4%) | 31.20 | (30.7) |
| | AL-2042 | 15.34 | |
| | water | 53.46 | |
| | | 100.0% | |
| 32. | X-105ᵉ (81.2%) | 6.16 | (510) |
| | AL-2042 | 2.50 | |
| | water | 91.34 | |
| | | 100.0% | |

*X-100 = the trimethylsulfonium salt of N-phosphonomethylglycine in aqueous solution
**a.i. refers to active ingredient
ªacid in aqueous solution
ᵇisopropylamine salt in aqueous solution
ᶜsodium salt in aqueous solution
ᵈammonium salt in aqueous solution
ᵉmagnesium salt in aqueous solution In addition to the PMCM compound and the surfactant, the composition can also include other conventional adjuvants such as heat stabilizers, ultraviolet absorbers, dispersants, and other agriculturally acceptable materials. Representative heat stabilizers include phenylenediamines, phenazine, butylated hydroxy toluene. Representative ultraviolet absorbers include Tinuvin 770, Tinuvin P, and dinitroanilines.

The ratio of PMCM compound to surfactant can vary over a wide range. Since it is known that the choice of a particular surfactant can affect the phytoactivity of the PMCM compounds used in accordance with this invention, the desired activity of the liquid composition should be considered when selecting a particular surfactant. As much surfactant as desired may be employed so long as the products dissolve totally or disperse readily in the diluent prior to application. For cost considerations, a minimum of surfactant should be used which still enables the objects of the invention to be obtained. The ratio of PMCM compound to surfactants by weight, is typically from about 10:1 to about 1:10. The preferred ratio is from about 4:1 to about 1:2. The most preferred ratio is from about 2:1 to about 1:1.

The compositions of this invention can be prepared in any suitable manner. A preferred process, however, comprises first preparing a mixture containing the PMCM compound and the dispersing agent. In preferred embodiments, the PMCM compound is dissolved in the agent. In other embodiments the PMCM compound is dispersed therein.

In some embodiments, the mixture is prepared by forming the PMCM compound in situ. For example, in some embodiments, N-phosphonomethylglycine is reacted with a desired base, in the presence of water, to form an aqueous solution containing the PMCM compound. In preferred embodiments, solutions of isopropylamine N-phosphonomethylglycine can be prepared in this manner.

The dispersing agent for use in accordance with the process of the invention must meet certain requirements. The agent must be capable of dissolving or dispersing a desired PMCM compound at the temperature used to form the initial mixture, without adversely effecting the PMCM compound's phytoactivity. The greater the solubility or ease or dispersability of the PMCM compound in the dispersing agent, the less agent will be required and the subsequent removal of agent will be facilitated.

Preferred dispersing agents include water and polar organic solvents, such as methanol, ethanol, isopropyl alcohol and acetone. Water is most preferred.

The herbicide compositions provided in accordance with this invention are effective when diluted with water and applied to the locus desired by spray or other means. The locus of application can be soil, seeds, seedlings, or the actual plants, as well as fettered fields. Foliar application is preferred. The compositions can be applied by the use of boom and hand sprayers, and can also be applied from airplane sprays because they are effective in very low dosages.

HERBICIDAL SCREENING TESTS

As previously mentioned, the herein described PMCM compounds are phytotoxic compounds which are useful and valuable in controlling various plant species. Selected compounds of this invention were tested as herbicides in the following manner.

Post-emergence herbicide test. On the tenth day preceding treatment, seeds of various weed species are planted in loamy sand soil in individual rows using one species per row across the width of a flat. The seeds used were Johnsongrass (*Echinochloa crusgalli*), annual morningglory (*Ipomoea lacunosa*), velvetleaf (*Abutilon theophrasti*), Bermudagrass (*Cynodon dactylon*), yellow nutsedge (*Cyperus esculentus*) and purple nutsedge (*Cyperus rotundus*). Ample seeds are planted to give about 20 to 40 seedlings per row, after emergence, depending upon the size of the plants.

A series of formulations were prepared by combining the trimethylsulfonium salt of N-phosphonomethylglycine (TMP) with various surfactants and water. In formulation No. 1 in the table which follows, the designation "TMP 4-LC (B)" refers to a formulation comprising 73.7 weight percent of an aqueous solution of the trimethylsulfonium salt of N-phosphonomethylglycine (55.9% active ingredient), 20.6 weight percent of a surfactant and 5.7 weight percent of water. In each of the other formulations set forth below, numerical correlation is made between the formulation and the formulations in the table. In the formulations set forth, the active ingredient (TMP) is indicated and adjacent thereto the percentage of active ingredient in the solution is set forth. Also, the surfactant is indicated as having a specific percent purity and this is set forth adjacent to the chemical name of the surfactant.

In the test procedure, each individual formulation was dissolved in water and various aliquots of water were used to dilute the concentration of the formulation so as to achieve the desired application rate.

After the desired dilution was obtained, a solution was then sprayed on a seeded flat on a linear spray table calibrated to deliver 80 gallons per acre (748 liters per hectare).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Tables.

TABLE 1

| Formulation | Formula | (a.i.) | lb/A | Johnsongrass Rep 1 | Johnsongrass Rep 2 | Bermudagrass Rep 1 | Bermudagrass Rep 2 | Purple Nutsedge Rep 1 | Purple Nutsedge Rep 2 |
|---|---|---|---|---|---|---|---|---|---|
| 1. TMP 57.5% | 71.7 | (41.2) | 1/4 | 85 | 95 | 40 | 50 | — | — |
| 4LC "B" (MP-5812) | 20.6 | (20.6) | 1/2 | 100 | 100 | 95 | 90 | 30 | 20 |
| water | 7.7 | | 1 | — | — | — | — | 90 | 90 |
| | 100.0% | | | | | | | | |
| 2. TMP 72% | 57.2 | (41.2) | 1/4 | 90 | 80 | 20 | 30 | — | — |
| APG 23-1 53% | 38.9 | (20.6) | 1/2 | 100 | 100 | 90 | 85 | 20 | 20 |
| water | 3.9 | | 1 | — | — | — | — | 90 | 70 |
| | 100.0% | | | | | | | | |
| 3. TMP 72% | 57.2 | (41.2) | 1/4 | 90 | 70 | 20 | 20 | — | — |
| APG 23-3 46% | 42.8 | (19.7) | 1/2 | 100 | 100 | 85 | 90 | 10 | 20 |
| water | 0.0 | | 1 | — | — | — | — | 85 | 70 |
| | 100.0% | | | | | | | | |
| 4. TMP 72% | 57.2 | (41.2) | 1/4 | 80 | 80 | 20 | 30 | — | — |
| APG 91-1 51% | 40.4 | (20.6) | 1/2 | 100 | 100 | 90 | 85 | 20 | 20 |
| water | 2.4 | | 1 | — | — | — | — | 80 | 70 |
| | 100.0% | | | | | | | | |
| 5. TMP 72% | 57.2 | (41.2) | 1/4 | 90 | 95 | 30 | 40 | — | — |
| APG 91-3 57% | 36.1 | (20.6) | 1/2 | 100 | 100 | 90 | 85 | 20 | 20 |
| water | 6.7 | | 1 | — | — | — | — | 90 | 80 |
| | 100.0% | | | | | | | | |
| 6. TMP 57.5% | 54.3 | (31.2) | 1/4 | 85 | 95 | 40 | 40 | — | — |
| APG 91-3 100% | 31.2 | | 1/2 | 100 | 100 | 90 | 93 | 20 | 20 |
| water | 14.5 | | 1 | — | — | — | — | 90 | 90 |
| | 100.0% | | | | | | | | |
| 7. TMP 57.5% | 54.3 | (31.2) | 1/4 | 80 | 90 | 10 | 0 | — | — |
| EMCOL D-7533 100% | 31.2 | (31.2) | 1/2 | 100 | 100 | 60 | 70 | 10 | 20 |
| water | 14.5 | | 1 | — | — | — | — | 80 | 70 |
| | 100.0% | | | | | | | | |
| 8. TMP 57.5% | 63.2 | (36.3) | 1/4 | 70 | 80 | 10 | 10 | — | — |
| AL-2041 | 27.3 | (27.3) | 1/2 | 98 | 100 | 90 | 80 | 30 | 20 |
| water | 9.5 | | 1 | — | — | — | — | 70 | 70 |
| | 100.0% | | | | | | | | |
| 9. TMP 57.5% | 63.2 | (36.3) | 1/4 | 70 | 90 | 10 | 10 | — | — |
| AL-2042 100% | 27.3 | (27.3) | 1/2 | 100 | 100 | 85 | 80 | 30 | 30 |
| water | 9.5 | | 1 | — | — | — | — | 70 | 80 |
| | 100.0% | | | | | | | | |
| 10. TMP 57.5% | 63.2 | (36.3) | 1/4 | 70 | 80 | 10 | 20 | — | — |
| APG 91-3 100% | 27.3 | (27.3) | 1/2 | 100 | 100 | 95 | 90 | 30 | 30 |
| water | 9.5 | | 1 | — | — | — | — | 70 | 90 |
| | 100.0% | | | | | | | | |
| 11. TMP 57.5% | 63.2 | (36.3) | 1/4 | 70 | 60 | 0 | 0 | — | — |

TABLE 1-continued

| Formulation | Formula | (a.i.) | lb/A | Johnsongrass Rep 1 | Rep 2 | Bermudagrass Rep 1 | Rep 2 | Purple Nutsedge Rep 1 | Rep 2 |
|---|---|---|---|---|---|---|---|---|---|
| EMCOL D-7533 100% | 27.3 | (27.3) | 1/2 | 100 | 90 | 60 | 60 | 0 | 0 |
| water | 9.5 | | 1 | — | — | — | — | 60 | 50 |
| | 100.0% | | | | | | | | |
| CHECK | | | 0 | 0 | 0 | 0 | 0 | 0 | 0 |

TABLE 2

| Formulation | Formula | (a.i.) | lb/A | Johnsongrass Rep 1 | Rep 2 | Bermudagrass Rep 1 | Rep 2 | Purple Nutsedge Rep 1 | Rep 2 |
|---|---|---|---|---|---|---|---|---|---|
| 1. TMP 57.5% | 71.7 | (41.2) | 1/4 | 100 | 100 | 40 | 50 | — | — |
| 4LC "B" (MP-5812) | 20.6 | (20.6) | 1/2 | 100 | 100 | 95 | 95 | 30 | 40 |
| water | 7.7 | | 1 | — | — | — | — | 85 | 95 |
| | 100.0% | | | | | | | | |
| 2. TMP 57.3% | 71.9 | (41.2) | 1/4 | 85 | 95 | 20 | 30 | — | — |
| AL 1685 100% | 20.6 | (20.6) | 1/2 | 100 | 100 | 80 | 90 | 30 | 40 |
| water | 7.5 | | 1 | — | — | — | — | 80 | 70 |
| | 100.0% | | | | | | | | |
| 3. TMP 57.3% | 71.9 | (41.2) | 1/4 | 85 | 95 | 20 | 20 | — | — |
| AL-2041 100% | 20.6 | (20.6) | 1/2 | 100 | 100 | 80 | 90 | 30 | 30 |
| water | 7.5 | | 1 | — | — | — | — | 85 | 85 |
| | 100.0% | | | | | | | | |
| 4. TMP 57.3% | 71.9 | (41.2) | 1/4 | 90 | 90 | 20 | 20 | — | — |
| AL-2042 100% | 20.6 | (20.6) | 1/2 | 90 | 100 | 70 | 90 | 30 | 20 |
| water | 7.5 | | 1 | — | — | — | — | 70 | 70 |
| | 100.0% | | | | | | | | |
| 5. TMP 57.3% | 71.9 | (41.2) | 1/4 | 70 | 70 | 30 | 30 | — | — |
| APG 91-3 100% | 20.6 | (20.6) | 1/2 | 100 | 95 | 90 | 90 | 20 | 10 |
| water | 7.5 | | 1 | — | — | — | — | 85 | 90 |
| | 100.0% | | | | | | | | |
| 6. TMP 57.5% | 54.3 | (31.2) | 1/4 | 95 | 90 | 20 | 30 | — | — |
| AL-2041 100% | 31.2 | (31.2) | 1/2 | 100 | 100 | 80 | 90 | 20 | 20 |
| water | 14.5 | | 1 | — | — | — | — | 70 | 90 |
| | 100.0% | | | | | | | | |
| 7. TMP 57.5% | 54.3 | (31.2) | 1/4 | 90 | 90 | 20 | 30 | — | — |
| AL-2042 100% | 31.2 | (31.2) | 1/2 | 100 | 100 | 90 | 90 | 20 | 20 |
| water | 14.5 | | 1 | — | — | — | — | 70 | 85 |
| | 100.0% | | | | | | | | |
| 8. TMP 57.3% | 71.9 | (41.2) | | | | | | | |
| APG 91-3 100% | 20.6 | | | | | | | | |
| water | 7.5 | | | | | | | | |
| | 100.0% | | | | | | | | |
| 9. TMP 57.3% | 71.9 | (41.2) | 1/4 | 70 | 60 | 40 | 40 | — | — |
| AL-1984 100% | 20.6 | | 1/2 | 98 | 95 | 95 | 90 | 30 | 40 |
| water | 7.5 | | 1 | — | — | — | — | 70 | 90 |
| | 100.0% | | | | | | | | |
| 10. TMP 57.3% | 71.9 | (41.2) | 1/4 | 50 | 50 | 20 | 30 | — | — |
| AL-1685 100% | 20.6 | | 1/2 | 90 | 95 | 90 | 90 | 30 | 20 |
| water | 7.5 | | 1 | — | — | — | — | 80 | 90 |
| | 100.0% | | | | | | | | |
| 11. TMP 57.3% | 71.9 | (41.2) | 1/4 | 70 | 60 | 30 | 30 | — | — |
| AL-2042 100% | 20.6 | | 1/2 | 90 | 100 | 90 | 90 | 30 | 30 |
| water | 7.5 | | 1 | — | — | — | — | 90 | 70 |
| | 100.0% | | | | | | | | |
| 12. TMP 57.3% | 71.9 | (41.2) | 1/4 | 50 | 50 | 10 | 10 | — | — |
| AL-2042 100% | 20.6 | | 1/2 | 80 | 100 | 85 | 95 | 20 | 30 |
| water | 7.5 | | 1 | — | — | — | — | 70 | 90 |

TABLE 2-continued

|  |  |  |  | Johnsongrass | | Bermudagrass | | Purple Nutsedge | |
|---|---|---|---|---|---|---|---|---|---|
| Formulation | Formula | (a.i.) | lb/A | Rep 1 | Rep 2 | Rep 1 | Rep 2 | Rep 1 | Rep 2 |
| CHECK | 100.0% |  | 0 | 0 | 0 | 0 | 0 |  |  |

TABLE 3

|  | Formulation | Formula | | Rate (lb/A) | Velvetleaf | Yellow Nutsedge | Annual Morningglory |
|---|---|---|---|---|---|---|---|
| 1. | TMP 57.3% | 71.9 | (41.2) | 1/2 | 40 | 40 | 40 |
|  | WITCAMIDE 272 100% | 20.6 |  | 1 | 70 | 70 | 100 |
|  | water | 7.5 |  | 2 | 95 | 90 | 100 |
| 2. | TMP 57.3% | 100.0% 71.9 | (41.2) | 1/2 | 30 | 30 | 30 |
|  | EMCOL D-7513 100% | 20.6 |  | 1 | 60 | 60 | 70 |
|  | water | 7.5 |  | 2 | 95 | 90 | 95 |
| 3. | TMP 57.3% | 100.0% 71.9 | (41.2) | 1/2 | 40 | 40 | 40 |
|  | EMCOL D-7533 100% | 20.6 |  | 1 | 70 | 70 | 100 |
|  | water | 7.5 |  | 2 | 98 | 95 | 100 |
| 4. | TMP 57.5% | 100.0% 71.7 | (41.2) | 1/2 | 40 | 50 | 30 |
|  | APG 23-3 100% | 20.6 | (9.5) | 1 | 60 | 90 | 50 |
|  | water | 7.7 |  | 12 | 90 | 100 | 80 |
| 5. | TMP 57.5% | 100.0% 71.7 | (41.2) | 1/2 | 30 | 40 | 30 |
|  | APG 91-1 51% | 20.6 | (10.5) | 1 | 60 | 70 | 50 |
|  | water | 7.7 |  | 2 | 90 | 100 | 80 |
| 6. | TMP 57.5% | 100.0% 71.7 | (41.2) | 1/2 | 40 | 50 | 30 |
|  | APG 91-3 57% | 20.6 | (11.7) | 1 | 80 | 90 | 50 |
|  | water | 7.7 |  | 2 | 100 | 100 | 80 |
|  | CHECK | 100.0% |  | 0 | 0 | 0 | 0 |
|  | CHECK |  |  | 0 | 0 | 0 | 0 |

Each of the formulations 28–32 was tested for herbicidal activity in accordance with the general procedure set forth below regarding herbicide tests.

The following quantities of each formulation were weighed into a 2 ounce bottle and sufficient water was added to achieve a volume of 40 milliliters (ml).

| Formulation 28 | 1.315 grams |
|---|---|
| Formulation 29 | 1.272 grams |
| Formulation 30 | 1.289 grams |
| Formulation 31 | 4.465 grams |
| Formulation 32 | 0.936 grams |

To achieve the desired application rates, each formulation was diluted with water in the following manner.

8.25 lb/A=5 ml +35 ml water (total 40 ml)

0.50 lb/A=10 ml +30 ml water (total 40 ml)

1.00 lb/A=20 ml +20 ml water (total 40 ml)

Forty milliliters of each of those solutions was applied post-emergence to the weed species utilizing a linear spray table at 25 gal/A using a 80015 nozzle set at 40 psi.

The soil used in these tests was a sandy loam soil from the Sunol, Calif. area.

The soil was treated by the addition of 17-17-17 fertilizer ($N$-$P_2O_5$-$K_2O$ on a weight basis), amounting to 50 ppm by weight, with respect to the soil, and CAPTAN®, a soil fungicide.

The thus treated soil was then placed in plastic tubs, 6 inches in diameter and 5 inches deep with drainage holes. Johnsongrass and quackgrass rhizomes, Bermuda grass cuttings and purple nutsedge tubers were planted in the test containers. The tests weeds were as follows: Johnsongrass (*Sorghum halepense*), Bermuda grass (*Cynodon dactylon*), purple nutsedge (*Cyperus rotundus*) and quackgrass (*Agropyron repens*).

Sufficient root stock or cuttings were planted to produce several weed plants per container. After planting, the containers were placed in a greenhouse maintained at 21° to 27° C. and surface watered daily with a sprinkler.

The formulations of N-phosphonomethylglycine were sprayed on the weeds approximately 35 days after planting.

Approximately 32 days after the spraying, the degree of weed control was rated and recorded as a percentage control compared to the control exhibited on the same species of the same age which had not been sprayed. The rating ranged from 0 to 100%, where 0 equaled no effect on plant growth when compared to the untreated control, and 100 equals complete killing of the test weeds.

The results of these tests are listed in Table 4.

TABLE 4

| Treatment | Rate (lb/A) | Johnson-grass | Bermuda-grass | Quack-grass | Purple Nut-sedge |
|---|---|---|---|---|---|
| Formulation 28 | 0.25 | 80 | 65 | 55 | — |
| | 0.5 | 100 | 100 | 98 | 40 |
| | 1.0 | — | — | — | 90 |
| Formulation 29 | 0.25 | 85 | 35 | 25 | — |
| | 0.5 | 100 | 75 | 65 | 40 |
| | 1.0 | — | — | — | 85 |
| Formulation 30 | 0.25 | 80 | 30 | 30 | — |
| | 0.5 | 100 | 80 | 90 | 30 |
| | 1.0 | — | — | — | 90 |
| Formulation 31 | 0.25 | 70 | 60 | 40 | — |
| | 0.5 | 100 | 85 | 95 | 35 |
| | 1.0 | — | — | — | 80 |
| Formulation 32 | 0.25 | 5 | 5 | 25 | — |
| | 0.5 | 40 | 20 | 50 | 5 |
| | 1.0 | — | — | — | 45 |
| Control | | 0 | 0 | 0 | 0 |

(—) indicates not tested at indicated rate.

The amount of the present composition which constitutes a herbicidally effective or phytoactive amount depends upon the nature of the seeds or plants to be controlled and the effect desired. The rate of application varies from about 0.01 to about 50 pounds per acre (a.i.), preferably from about 0.1 to about 25 pounds per acre (a.i.), with the actual amount depending on the overall cost and the desired results. It will be readily apparent to one skilled in the art that compositions exhibiting local herbicidal activity will require a higher dosage than more active compounds for the same degree of control.

As used herein, the term "herbicide" refers to a compound which controls or modifies plant growth, e.g., killing, retarding, defoliating, desiccating, regulating, stunting, tillering and dwarfing. "Plant" refers to all physical parts, including seeds, seedlings, saplings, roots, tubers, stems, stalks, foliage and fruits. "Plant growth" is meant to include all phases of development from seed germination to natural or induces cessation of life.

What is claimed is:

1. A liquid phytoactive composition comprising:

(a) an herbicidally effective, agriculturally acceptable salt of an N-phosphonomethyl-N-carboxymethyl compound;

(b) one or more liquid nonionic alkyl polyglycoside surfactants;

(c) a dispersing medium selected from the group consisting of water and polar organic solvents for said N-phosphonomethyl-N-carboxymethyl compound; and (d) an insert adjuvant.

2. A liquid phytoactive composition in the form of a liquid concentrate comprising:

(a) from about 10 to about 70 weight percent of an herbicidally effective, agriculturally acceptable salt of an N-phosphonomethyl-N-carboxymethyl compound;

(b) from about 40 weight percent of one or more water-soluble non-irritating, non-toxic liquid nonionic alkyl polyglycoside surfactants;

(c) from about 10 to about 40 weight percent of a dispersing medium selected from the group consisting of water and polar organic solvents for said N-phosphonomethyl-N-carboxymethyl compound; and (d) from about 0.5 to about 10 weight percent of inert adjuvants.

3. A composition according to claim 2 wherein the N-phosphonomethyl-N-carboxymethyl compound is of the formula

and wherein M is independently selected from hydrogen and agriculturally acceptable salt-forming moieties.

4. A composition according to claim 3 wherein at least one M is selected from an agriculturally acceptable salt-forming moiety.

5. The composition of claim 2 wherein the N-phosphonomethyl-N-carboxymethyl compound is N-phosphonomethylglycine.

6. The composition of claim 2 wherein the N-phosphonomethyl-N-carboxymethyl compound is the trimethylsulfonium salt of N-phosphonomethylglycine.

7. The composition of claim 2 wherein the N-phosphonomethyl-N-carboxymethyl compound is the isopropylamine salt of N-phosphonomethylglycine.

8. The composition of claim 2 wherein the N-phosphonomethyl-N-carboxymethyl compound is the sodium salt of N-phosphonamethylglycine.

9. The composition of claim 2 wherein the N-phosphonomethyl-N-carboxymethyl compound is the ammonium salt of N-phosphonamethylglycine.

10. The composition of claim 2 wherein the N-phosphonomethyl-N-carboxymethyl compound is the magnesium salt of N-phosphonomethylglycine.

11. The composition of claim 2 wherein the surfactant is a mixed alcohol glucoside.

12. The composition of claim 2 wherein (d) contains one or more of an anti-foaming agent, a heat stabilizing agent and an ultraviolet absorber.

* * * * *